US009949983B2

(12) United States Patent
Chipkin

(10) Patent No.: US 9,949,983 B2
(45) Date of Patent: Apr. 24, 2018

(54) FUSED BENZAZEPINES FOR TREATMENT OF STUTTERING

(71) Applicant: PSYADON PHARMACEUTICALS, INC., Germantown, MD (US)

(72) Inventor: Richard E. Chipkin, Bethesda, MD (US)

(73) Assignee: Psyadon Pharmaceuticals, Inc., Germantown, MD (US)

( * ) Notice: Subject to any disclaimer, the term of this patent is extended or adjusted under 35 U.S.C. 154(b) by 0 days.

(21) Appl. No.: 15/030,271

(22) PCT Filed: Oct. 17, 2014

(86) PCT No.: PCT/US2014/061080
§ 371 (c)(1),
(2) Date: Apr. 18, 2016

(87) PCT Pub. No.: WO2015/058053
PCT Pub. Date: Apr. 23, 2015

(65) Prior Publication Data
US 2016/0271141 A1 Sep. 22, 2016

Related U.S. Application Data

(60) Provisional application No. 61/892,841, filed on Oct. 18, 2013.

(51) Int. Cl.
*A61K 31/55* (2006.01)
*A61K 45/06* (2006.01)
*A61K 9/00* (2006.01)
*A61K 31/519* (2006.01)

(52) U.S. Cl.
CPC ............ *A61K 31/55* (2013.01); *A61K 9/0053* (2013.01); *A61K 31/519* (2013.01); *A61K 45/06* (2013.01)

(58) Field of Classification Search
None
See application file for complete search history.

(56) References Cited

U.S. PATENT DOCUMENTS

| 4,477,378 A | 10/1984 | Gold et al. |
| 4,973,586 A | 11/1990 | Berger et al. |
| 5,302,716 A | 4/1994 | Berger et al. |

FOREIGN PATENT DOCUMENTS

| WO | WO 93/01702 | 1/1993 |
| WO | WO 93/13073 | 7/1993 |
| WO | WO 95/25102 | 9/1995 |
| WO | WO 99/021540 A2 | 5/1999 |
| WO | WO 2012/033874 A1 | 3/2012 |

OTHER PUBLICATIONS

VanHole, Nicholas. Shared Consciousness: A Social History of Tourette Syndrome and its Treatments. University of Montana. ScholarWorks at University of Montana. Theses, Dissertations, Professional Papers. 2012, 123 pages.*
Ashurst, John et al., Developmental and Persistent Developmental Stuttering: An Overview for Primary Care Physicians, Journal of American Osteopathic Associations, 111, 576-580, 2011.
Blomgren, Michael, Behavioral Treatments for Children and Adults Who Stutter: a Review, Psychol. Res. Behav. Management, 6:9-19, 2013.
Bothe, AK et al., Stuttering Treatment Research 1970-2005. I: Systematic Review Incorporating Trial Quality Assessment of Behavioral, Cognitive, and Related Approaches, American Journal of Speech-Language Pathology, 15:321-341, 2006.
Boyd, A et al., Pharmacological Agents for Developmental Stuttering in Children and Adolescents: A Systemic Review, J. Clin. Psychopharmacol., 31(6):740-744, 2011.
Buchel, Christian et al., What Causes Stuttering?, PLoS Biology, 2(2):159-163, 2004.
Chipkin, R.E. et al., Pharmacological Profile of SCH39166: a Dopamine D1 Selective Benzonaphthazepine With Potential Antipsychotic Activity, J. Pharmacol. Exp. Ther., 247:1092-1102, 1988.
Civelli, O. et al., Molecular Diversity of the Dopamine Receptors. Ann. Rev. Pharmacol. Toxicol. 32:281-307, 1993.
Costa, Daniel et al., Stuttering: an Update for Physicians, Canadian Medical Association Journal, 162:1849-1855, 2000.
Emilien, G. et al., Dopamine Receptors—Physiological Understanding to Therapeutic Intervention Potential. Pharmacol. Therap. 84:133-156, 1999.
European Search Report issued in connection with corresponding European Patent Application No. 14854586.6, dated Sep. 5, 2017, 10 pages.
Kraft, SJ et al., Genetic Bases of Stuttering: The State of the Art, 2011, Folia Phoniatr Logop, 64(1):34-47, 2012.
Haile, Colin et al., The Dopamine D1 Receptor Agonist SKF-82958 Serves as a Discriminative Stimulus in the Rat, Eur. J. Pharmacol., 388(2): 125-131, 2000.
Ingham, Roger et al., Towards a Functional Neural Systems Model of Developmental Stuttering, J. Fluency Disord., 28(4):297-317, 2003.
Karlsson et al., Karlsson, P. et al., Evaluation of SCH 39166 as PET Ligand for Central D1 Dopamine Receptor Binding and Occupancy in Man., Psychopharmacol., 121(3):300-308, 1995.

(Continued)

*Primary Examiner* — Samantha L Shterengarts
(74) *Attorney, Agent, or Firm* — Duane Morris LLP; Vicki G. Norton

(57) ABSTRACT

The present invention encompasses methods of treating a subject who stutters. The methods can include the steps of: (a) identifying a subject in need of treatment; and (b) administering to the subject a therapeutically effective amount of a composition comprising a D1/D5 receptor antagonist, a D1/D5 receptor partial agonist, or a mixture thereof. For example, the D1/D5 receptor antagonist can be ecopipam or a pharmaceutically acceptable salt, solvate, hydrate, prodrug, structural analog, metabolite, or polymorph thereof.

20 Claims, No Drawings

(56) References Cited

OTHER PUBLICATIONS

Maguire, Gerald et al., Risperidone for the Treatment of Stuttering, Journal of Clinical Psychopharmacology, vol. 20, No. 4, 479-482, Aug. 2000.

Maguire, Gerald et al., Alleviating Stuttering with Pharmacological Interventions, Expert Opinion on Pharmacotherapy, vol. 5, No. 7, 1565-1571, Jan. 2004.

Maguire, G. et al., Exploratory Randomized Clinical Study of Pagoclone in Persistent Developmental Stuttering: The Examining Pagoclone for Persistent Developmental Stuttering Study., J. Clin. Psychopharmacol. 30:48-56, 2010.

McQuade,, Robert et al., [3H]SCH 39166, A New D1-Selective Radioligand: In Vitro and In Vivo Binding Analyses, Journal of Neurochemistry, 57(6), 2001-2010, 1991.

Newbury, D.F. et al., Genetic Advances in the Study of Speech and Language Disorders, Neuron, 68:309-320, 2010.

Pettersson, Ingrid et al., A Study on the Contribution of the 1-Phenyl Substituent to the Molecular Electrostatic Potentials of Some Benzazepines in Relation to Selective Dopamine D-1 Receptor Activity, J. Med. Chem., vol. 35, 502-507, 1992.

Prasse, Jane et al., Stuttering: An Overview, American Family Physician, 77:1271-1276, 2008.

Risperidone, Wikipedia, Mar. 31, 2017, Retrieved from the Internet: URL:https://en.wikipedia.org/wiki/Risperidone, 17 Pages.

Shah, Jamshed et al., (.+−.)-(Aminoalkyl)benzazepine Analogs: Novel Dopamine D1 Receptor Antagonists, J. Med. Chem., 38(21):4284-4293, 1995.

Shaygannejad Shaygannejad, Vahid et al., Olanzapine Versus Haloperidol: Which Can Control Stuttering Better?, Int J Prev Med. 4(Suppl 2):S270-273, 2013.

Zypadhera, European Medicines Agency, Apr. 25, 2014, XP002769139, 7 Pages.

* cited by examiner

FUSED BENZAZEPINES FOR TREATMENT OF STUTTERING

CROSS-REFERENCE TO RELATED APPLICATIONS

This application is a 371 National Phase of International Application No. PCT/US2014/061080, which was filed on Oct. 17, 2014 and claims the benefit of the filing date of U.S. Provisional Application No. 61/892,841, filed Oct. 18, 2013, the contents of each of which are hereby incorporated by reference in their entirety.

FIELD OF THE INVENTION

This invention relates to methods of treating patients suffering from stuttering, and more particularly to the treatment of stuttering with fused benzazepines.

BACKGROUND

The International Classification of Diseases 2010 (ICD-10) defines stuttering, which is also called stammering, as "[s]peech that is characterized by frequent repetition or prolongation of sounds or syllables or words, or by frequent hesitations or pauses that disrupt the rhythmic flow of speech." Stuttering is classified as a disorder when it markedly disturbs the fluency of speech. Typically, the disorder includes repeated articulatory movements (e.g., t-t-t-talk) and/or fixed articulatory movements (e.g., mmm-mine). Verbal interjections (e.g., "um" or "like") are common. Verbal signs can be accompanied by nonverbal signs, including facial grimaces, excessive eye blinking, muscle tension, odd movements of the head, and struggling to speak. These behaviors may be learned approaches to minimize the severity of a stutter. People who stutter often experience emotional distress, and anxiety can cause them to avoid educational and social situations that they would otherwise enjoy and benefit from.

The neurophysiological basis of stuttering is thought to share some similarities with other movement disorders. Specifically, stuttering may arise due to abnormal signaling in one or more of the circuits between the cortex, striatum, globus pallidus, and thalamus (the cortical-striatal-pallidal-thalamo or CSPT circuit). Circuit models have implied that excess dopamine activation increases unwanted movements of the muscles controlling speech (at D1 receptors) and, conversely, that dopamine blockade (at D2 receptors) promotes unwanted movements. Known D2 antagonists like clozapine, olanzapine, asenapine, and risperidone have all been reported to induce stuttering (Grover et al., 2012; Bar et al., 2004; Yaday, 2010; Maguire et al., 2011) and D2-preferring dopamine agonists such as methylphenidate have been reported to relieve stuttering (Devroey et al., 2012).

We are unaware of any treatments approved by any recognized government regulatory authority for the treatment of stuttering. Most patients are treated with behavioral techniques (see Blomgren, *Psychol. Res. Behav. Management*, 6:9-19, 2013). When used in severely afflicted patients, pharmacotherapy typically involves drugs for the treatment of anxiety (see, e.g., Maguire et al., *J. Clin. Psychopharmacol.* 30:48-56, 2010). This is based on the observation that stress exacerbates stuttering and the assumption that reducing stress will relieve some symptoms.

Several review articles concerning stuttering are available. These include: Boyd et al., *J. Clin. Psychopharmacol.*, 31:740-744, 2011; Ingham, et al., *J. Fluency Disord.*, 28:297-317, 2003; Maguire et al., *Expert Opin. Pharmacother.*, 5:1565-1571, 2004; Kraft and Yairi, *Folia Phoniatrica et Logopaedica*, 64:34-47; Ashert and Wasson, *Journal of American Osteopathic Association*, 111:576-580; Newbury and Monaco, *Neuron*, 68:309-320; Prasse and Kikano, *American Family Physician*, 77:1271-1276, 2008; Büchel and Sommer, *PLoS Biology*, 2:159-163; Bothe et al., *American Journal of Speech-Language Pathology*, 15:321-341, 2005; Costa and Kroll, *Canadian Medical Association Journal*, 162:1849-1855, 2000; and Ashert and Wasson, *Journal of American Osteopathic Association*, 111:576-580, 2011).

SUMMARY

The present invention is based, in part, on the use of compounds that selectively bind the D1/D5 receptor and subsequently inhibit dopamine access to the D1/D5 receptor in the treatment of (e.g., the amelioration of) one or more of the signs or symptoms associated with CSPT circuit disorders. In one embodiment, the sign or symptom is stuttering. Accordingly, the present invention encompasses methods of treating a subject who stutters or stammers. The methods can include the steps of: (a) identifying a subject in need of treatment; and (b) administering to the subject a therapeutically effective amount of a composition comprising a D1/D5 receptor antagonist, a D1/D5 receptor partial agonist, or a mixture thereof. The subject can be a human and can be of any age (e.g., a young child of about 2-4 years old; an older child or young adult of about 17, 18, or 21 years old, or an older person who is at least 17, 18, or 21 years old). It is believed that about 1% of the global population of all ages, ethnicities, and cultures stutter, and patients of any age or ethnicity can be treated as described herein.

The subject in need of treatment may have been diagnosed as having developmental, neurogenic, or psychogenic stuttering (the latter two are also referred to as acquired stuttering). Developmental stuttering usually occurs at the beginning of words and non-verbal, secondary behaviors may be more pronounced than they are with acquired stuttering. Developmental stuttering manifests during the period of extensive speech and language development. Its onset is usually gradual, occurring between about 3 and 8 years of age, and spontaneous remission can occur within about four years. In a minority of children, there is no spontaneous resolution or relief from speech therapy, leaving them with persistent developmental stuttering that requires further intervention.

In other embodiments, the subject in need of treatment has been diagnosed as having neurogenic stuttering, which is triggered by brain damage. More specifically, neurogenic stuttering can be caused by a traumatic head and/or brain injury, a stroke or any type of vascular blockage or bleeding within the brain (e.g., an intracerebral hemorrhage), a neurodegenerative disease such as Alzheimer's disease or Creutzfeldt-Jacob disease, or any encephalopathy. Psychogenic stuttering is characterized by the rapid repetition of the initial sounds of a word, and it is seen in adults with a history of psychological illness or emotional trauma. Accordingly, patients amenable to treatment include those who develop a stutter secondary to brain damage or in the context of a psychological illness or emotional trauma.

The D1/D5 receptor antagonist can be ecopipam or a pharmaceutically acceptable salt, solvate, hydrate, prodrug, structural analog, metabolite, or polymorph thereof. In the course of this application, we may provide lists such as this one. It is to be understood that only one item may be selected; that a combination of items may be selected; and that one or more of the listed items may be purposefully excluded. For example, a formulation useful as described herein can include ecopipam; a pharmaceutically acceptable salt of ecopipam; or a mixture of ecopipam and a pharmaceutically acceptable salt thereof. Further, any of these alternatives can explicitly exclude any other listed item. For example, a formulation useful as described herein can include ecopipam but exclude a structural analog thereof.

The compound administered (e.g., a D1/D5 receptor antagonist) can be formulated for oral delivery (e.g., formulated in a unit dosage form of about 0.01 mg/kg to about 500 mg/kg (e.g., about 0.01 mg/kg to about 50 mg/kg; about 0.01 mg/kg to about 5 mg/kg; or about 0.1 mg/kg to about 5 mg/kg)). With respect to daily dosages, the compound administered (e.g., a D1/D5 receptor antagonist) can be administered at a dose of about 5 to about 100 mg/day, about 5 to about 50 mg/day or about 50 to about 100 mg/day. The administration can occur once per day or in divided doses, and any of the treatments described herein can include a step of administering a distinct, "second" treatment for treating the stuttering. For example, the methods of the invention encompass administration of a compound as described herein together with a behavioral therapy, surgical therapy, or distinct pharmaceutical therapy.

The present invention can be described in terms of "use" and encompasses use of a compound as described herein in the preparation of a medicament for the treatment of stuttering. The compound within the medicament can be a D1/D5 receptor antagonist, a D1/D5 receptor partial agonist, or a mixture thereof, and the specific formulation can be as described further herein.

The details of one or more embodiments of the invention are set forth in the accompanying drawings and the description below. Other features, objects, and advantages of the invention will be apparent from the description and drawings, and from the claims.

DETAILED DESCRIPTION

The present invention is based, in part, on the use of compounds that selectively bind the D1/D5 receptor and subsequently inhibit dopamine access to the D1/D5 receptor in the treatment of (e.g., the amelioration of) one or more of the signs or symptoms associated with CSPT circuit disorders. In one embodiment, the sign or symptom is stuttering. Accordingly, the methods of the invention encompass the administration of pharmaceutical formulations including selective D1/D5 antagonists to a patient who stutters. As secondary neurologic deficits result from speech disorders of a certain severity, including stuttering, the present methods can also provide relief from these downstream events. The therapeutic methods described herein can be carried out in connection with other therapies such as behavioral, pharmacologic, and surgical therapies (e.g., in the event the stuttering arises from a brain injury) that are designed to reduce the frequency or severity of the verbal and/or nonverbal signs of stuttering or to increase a patient's ability to cope. The methods can also be carried out following or in connection with genetic testing. Several genetic studies have identified linkage to numerous loci across the genome, spanning about a dozen chromosomes. Several genes and certain specific mutations are reviewed by Kraft and Yairi (*Folia Phoniatrica et Logopaedica*, 64:34-47, 2012; see also Newbury and Monaco, *Neuron*, 68:309-320, 2010). The accompanying therapy or process may also include imaging. Neuroimaging and studies involving certain dopamine receptor antagonists support the theory of a hyperdopaminergic origin of stuttering. A number of clinical trials for stuttering have been carried out for various drugs and have shown variable degrees of efficacy (reviewed by Bothe et al., *American Journal of Speech-Language Pathology*, 15:321-341, 2005). Certain drugs approved to treat conditions like epilepsy, anxiety, and depression have been used to treat stuttering but these drugs often have severe side effects making their long-term use difficult.

Compositions suitable for use in the present methods include compounds that selectively bind to the D1 and/or the D5 receptor and pharmaceutical compositions containing such compounds. As is known in the art, dopamine is a neurotransmitter active within the central nervous system, and its receptors have been classified into two families based on their genetic structure: the D1 family including the subtypes D1 and D5, and the D2-family including the subtypes D2, D3, and D4 (see, e.g., Civelli et al., *Ann. Rev. Pharmacol. Toxicol.* 32:281-307, 1993; and Emillien et al., *Pharmacol. Therap.* 84:133-156, 1999).

Although there are no universally accepted criteria, compounds are typically said to be selective for one receptor over another when their binding affinities are at least 100-fold different. Compounds are also defined as being agonists or antagonists according to their actions at the receptor. With respect to the neurotransmitter dopamine, pure agonists completely mimic the effects of the native neurotransmitter; pure antagonists completely block the actions of an agonist while having no agonist activity of their own; and partial agonists can exhibit mixed actions, showing some degree of intrinsic positive activity at the receptor (albeit less than what would be seen with the native neurotransmitter) while also blocking the actions of an agonist under some conditions.

Compounds useful in the context of the present invention include pure and/or selective D1 receptor antagonists, pure and/or selective D5 antagonists, pure and/or selective D1/D5 receptor antagonists, selective partial antagonists of the D1 receptor, selective partial agonists of the D5 receptor, and selective partial agonists at the D1/D5 receptor. Such compounds can be used alone or in any combination; in some embodiments, the compositions can include a mixture of two or more such compounds in equal or unequal amounts.

The compounds can conform to the generic formula in the table below.

TABLE I

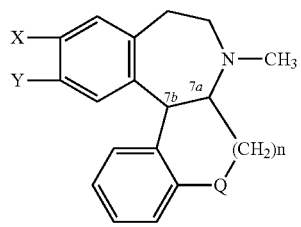

| Col. 1 | Col. 2 | Col. 3 stereo-chemistry | Col. 4 | Col. 5 | Col. 6 Ki (nM) | Col. 7 Ki (nM) | Col. 8 |
|---|---|---|---|---|---|---|---|
| Q | n | of 7a and 7b H's | X | Y | $^3$H-23390 | $^3$H-Spip | CAR (MED) |
| $CH_2$ | 1 | cis | $CH_2O$ | OH | 6450 | >100,000 | |
| $CH_2$ | 1 | cis | HO | $CH_3O$ | 44,800 | >100,000 | |
| $CH_2$ | 1 | trans | $CH_3O$ | OH | 23 | 2500 | 30 (po); 0.3-1 (sc) |
| $CH_2$ | 1 | trans | HO | $CH_3O$ | 2970 | >100,000 | |
| $CH_2$ | 1 | trans | Cl | OH | 5.5 | 11,500 | 30 (po); 0.3 (sc) |
| $CH_2$ | 1 | 7b(S):7a(R)(+) | Cl | OH | 1800 | >100,000 | >30 (po) |
| $CH_2$ | 1 | 7b(R): 7a(S)(−) | Cl | OH | 12 | 14,300 | 30 (po) |
| $CH_2$ | 1 | cis | Cl | OH | 6200 | >100,000 | |
| $CH_2$ | 1 | trans | H | OH | 30 | 3500 | |
| $CH_2$ | 2 | trans | $CH_3O$ | OH | 292 | >100,000 | 10 (sc) |
| $CH_2$ | 2 | trans | HO | $CH_3O$ | 7730 | >100,000 | 10 (sc) |
| $CH_2$ | 1 | trans | $CH_3$ | OH | 119 | 7200 | |
| $CH_2$ | 1 | trans | Cl | $NH_2$ | 70 | 4175 | 3 (po) |
| O | 1 | trans | H | OH | 121 | — | |
| $CH_2$ | 0 | trans | Cl | OH | 10 | 2600 | |

Such compounds are known in the art and are more fully described in U.S. Pat. No. 4,973,586, which is hereby incorporated by reference in its entirety.

In one embodiment, the compound can be a metabolite of ecopipam or another compound described herein. For example, the compound can be a desmethyl compound, such as the desmethyl form of ecopipam, which has been referenced in the art as SCH 40853.

More specifically, the compound can be:
1) 6,7,7a,8,9,13b-hexahydro-2-hydroxy-3-methoxy-7-methyl-5H-benzo[d]naphtho[2,1-b]azepine;
2) 6,7,7a,8,9,13b-hexahydro-2-hydroxy-7-methyl-5H-benzo[d]naphtho[2,1-b]azepine;
3) 6,7,7a,8,9,13b-hexahydro-3-chloro-2-hydroxy-7-methyl-5H-benzo[d]naphtho[2,1-b]azepine;
4) 6,7,7a,8,9,13b-hexahydro-2-hydroxy-3,7-dimethyl-5H-benzo[d]naphtho[2,1-b]azepine;
5) 6,7,7a,8,9,13b-hexahydro-2-amino-7-methyl-5H-benzo[d]naphtho[2,1-b]azepine;
6) 6,7,7a,8,9,13b-hexahydro-2-amino-3-chloro-7-methyl-5H-benzo[d]naphtho[2,1-b]azepine;
7) 6,7,7a,8,9,13b-hexahydro-2-amino-3,7-dimethyl-5H-benzo[d]naphtho[2,1-b]azepine;
8) 6,6a,7,8,9,13b-hexahydro-12-methoxy-7-methyl[1]benzopyrano[4,3-a][3]benzazepine;
9) 6,6a,7,8,9,13b-hexahydro-7-methyl[1]benzopyrano[4,3-a][3]benzazepin-12-ol;
10) 6,6a,7,8,9,13b-hexahydro-3-chloro-2-methoxy-7-methyl-5H-benzo[d]naphtho[2,1-b]azepine;
11) 2-hydroxy-3-methoxy-7-methyl-5,6,7,7a,8,9,10,14b-octahydro-benzo[d]benzo[3,4]cyclo-hepta[1,2-b]azepine;
12) 3-hydroxy-2-methoxy-7-methyl-5,6,7,7a,8,9,10,14b-octahydro-benzo[d]benzo[3,4]cyclo-hepta[1,2-b]azepine;
13) 5,6,7,7a,8,12b-hexahydro-2-hydroxy-3-chloro-7-methyl-benz[d]indeno[2,1-b]azepine;
14) 5,6,7,7a,8,12b-hexahydro-2-hydroxy-3-methoxy-7-methyl-benz[d]indeno[2,1-b]azepine;
15) 5,6,7,7a,8,12b-hexahydro-2-amino-3-chloro-7-methyl-benz[d]indeno[2,1-b]azepine;
16) 5,6,7,7a,8,12b-hexahydro-2-hydroxy-7-methyl-benz[d]indeno[2,1-b]azepine;
17) 5,6,7,7a,8,12b-hexahydro-3,7-dimethyl-2-hydroxy-benz[d]indeno[2,1-b]azepine;
18) 5,6,7,7a,8,12b-hexahydro-3-chloro-7-cyclopropylmethyl-2-hydroxy-benz[d]indeno[2,1b]azepine;
19) 5,6,7,7a,8,12b-hexahydro-7-allyl-3-chloro-2-hydroxy-benz[d]indeno[2,1-b]azepine;
20) 5,6,7,7a,8,12b-hexahydro-3-chloro-2-hydroxy-7,8,8-trimethyl-benz[d]indeno[2,1-b]azepine;
21) 5,6,7,7a,8,11b-hexahydro-3-chloro-7-methylthieno[2',3':4,5]cyclopenta[1,2-a][3]benzazepine-2-ol;
22) 5,6,7,7a,8,12b-hexahydro-2-hydroxy-3-chloro-benz[d]indeno[2,1-b]azepine;
23) 6,7,7a,8,9,13b-hexahydro-3-chloro-2-hydroxy-5H-benzo[d]naphtho[2,1-b]azepine; or
24) 6,7,7a,8,9,13b-hexahydro-2-amino-3-trifluoromethyl-7-methyl-5H-benzo[d]naphtho[2,1-b]azepine.

As noted elsewhere herein the compound administered can be in the form of a pharmaceutically acceptable salt and/or a trans isomer. An exemplary D1/D5 receptor antagonist useful in the methods of the invention is SCH39166, which is also known as PSYRX101 or ecopipam (6,7,7a,8,9,13b-hexahydro-3-chloro-2-hydroxy-5H-benzo[d]naphtho[2,1-b]azepine or, in trans form, (−)-trans-6,7,7a,8,9,13b-hexahydro-3-chloro-2-hydroxy-5H-benzo[d]naphtho[2,1-b]azepine). Ecopipam conforms to the structure:

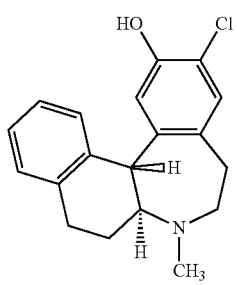

SCH 39166

In vitro binding studies using rat brain homogenates show that ecopipam has high affinity for D1/D5 receptors at low concentrations (see Chipkin et al., *J. Pharmacol. Exp. Ther.*, 247:1092-1102, 1988; and McQuade et al., *J. Neurochem.*, 57:2001-2010, 1991). Additional binding studies versus D2-selective ligands ($^3$H-spiperone) showed that ecopipam was roughly 1000-fold selective for the D1 vs. the D2 receptor, and 100-fold selective versus the serotonin receptor (versus $^3$H-ketanserin). Moreover, it did not bind at concentrations >700-fold to any of the following sites: adenosine, benzodiazepine, glutamate/AMPA/kainate, GABA, muscarinic, nicotinic, opiate, or alpha- or beta-adrenergic sites.

Activation of D1 receptors by dopamine and similar agonists stimulates the production of cyclic AMP (cAMP) via activation of adenylate cyclase. In vitro studies on this neuronal second messenger confirmed that ecopipam was an antagonist. In vivo studies on dopamine-agonist-induced behaviors (e.g., selective D1-agonist discriminative stimulus conditions in rats) likewise showed that ecopipam was a selective D1 antagonist in animals (Haile et al., *Eur. J. Pharmacol.*, 38:125-131, 2000). To ensure that there was no species specificity to the receptor binding profile, ecopipam's potency and selectivity were evaluated using cloned human receptors. Ecopipam bound with high affinity to hD1/hD5 receptors, but was >700-fold selective versus the hD2, hD3, and hD4 receptors. Positron emission tomography (PET) studies using radiolabeled ecopipam have been conducted in healthy volunteers (Karlsson et al., *Psychopharmacol.*, 121:300-308, 1995). The results showed specific binding in the human brain, and that binding corresponded to the known distribution of dopamine D1 receptors.

Other exemplary D1/D5 receptor antagonists that are useful in the present methods include: SCH23390 and compounds related thereto, including SCH 12679 and the compounds described in U.S. Pat. No. 4,477,378 (which is hereby incorporated by reference in the present application in its entirety), BTS-73-947, NNC-22-0010, JHS-271, JHS-198, JHS-136, A69024, and NNC687. Exemplary D1/D5 partial agonists include SKF38393, fenoldapam; SKF75670A; SKF 81297; SKF82958; and dinapsoline.

The structures of some of these compounds are illustrated here:

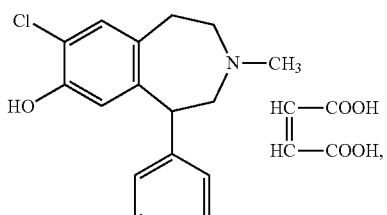

SCH 23390

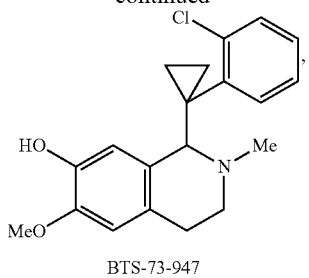

BTS-73-947

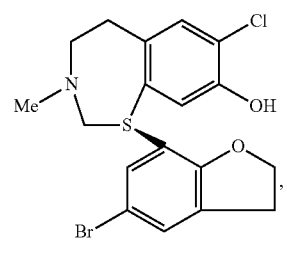

NNC-22-0010

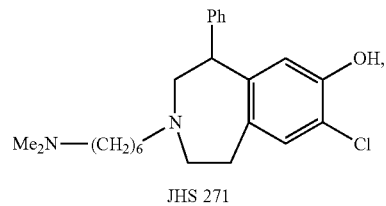

JHS 271

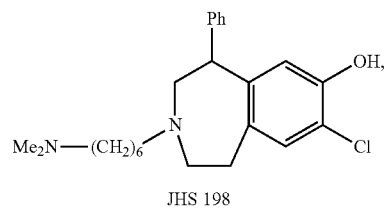

JHS 198

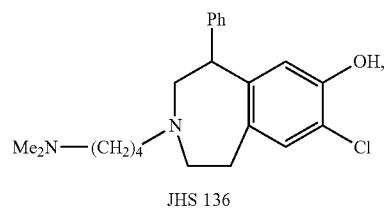

JHS 136

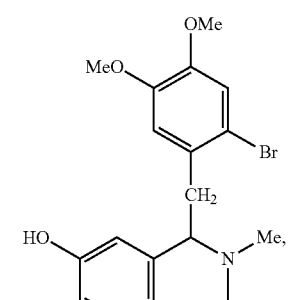

A 69024

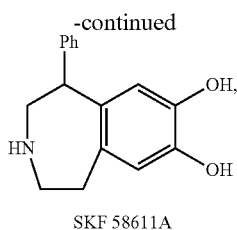

SKF 58611A

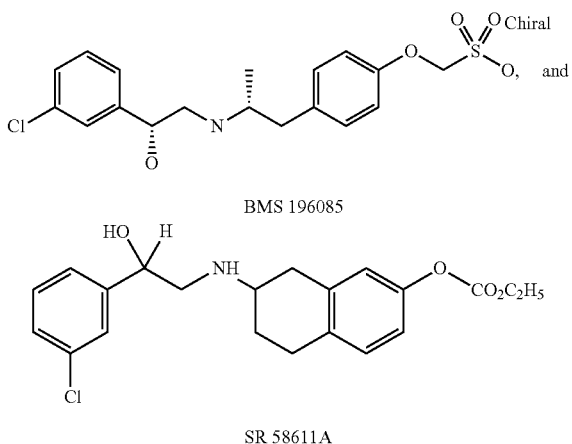

BMS 196085

SR 58611A

This invention also relates to pharmaceutically acceptable salts, solvate, hydrate, prodrug, structural analog, metabolite, or polymorphs of any of the foregoing compounds, or any other compounds described herein.

The chemical names of these compounds appear in the following Table:

| | |
|---|---|
| SCH 39166 (ecopipam) | (−)-trans-6,7,7a,8,9,13b-hexahydro-3-chloro-2-hydroxy-N-methyl-5H-benzo [d]-naphtho-[2,1-b]azepine |
| SCH 23390 | (d)-7-chloro-8-hydroxy-3-methyl-1-phenyl-2,3,4,5-tetrahydro-1H-3-benzazepine maleate |
| BTS-73-947 | 1-[1-(2-chlorophenyl)cyclopropyl]-1,2,3,4-tetrahydro-7-hydroxy-6-methoxy-2-methyl-(S)-isoquinolinol |
| NNC-22-0010 | (+)-5-(5-bromo-2,3-dihydro-7-benzofuranyl)-8-chloro-2,3,4,5-tetrahydro-3-methyl-1H-3-benzazepin-7-ol |
| JHS-271 | 8-chloro-3-[6-(dimethylamino)hexyl]-2,3,4,5-tetrahydro-5-phenyl-1H-3-benzazepin-7-ol |
| JHS-198 | 8-chloro-3-[6-(dimethylamino)hexyl]2,3,4,5-tetrahydro-5-phenyl-1H-3-benzazepin-7-ol with boranecarbonitrile (1:1). |
| JHS-136 | 8-chloro-3-[4-(dimethylamino)butyl]-2,3,4,5-tetrahydro-5-phenyl-1H-3-benzazepin-7-ol |
| A-69024 | 1-[(2-bromo-4,5-dimethoxyphenyl)methyl]-1,2,3,4-tetrahydro-6-methoxy-2-methyl-7-isoquinolinol |

Compounds useful in the present invention can be prepared in a variety of ways known to one of ordinary skill in the art of organic synthesis. Starting materials are readily available, and it will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures. Thus, the foregoing D1/D5 antagonists can be prepared by known methods. For example, one of ordinary skill in the art could synthesize compounds by the methods described in U.S. Pat. No. 5,302,716, which is hereby incorporated by reference in its entirety, and such compounds are useful in the present methods. One could also consult the published PCT applications WO 93/13073; WO 93/1702; WO 95/25102. One could also consult *J. Med. Chem.*, 38(21):4284-4293, 1995. An exemplary D1/D5 partial agonist is SKF 38393, having the chemical name 2,3,4,5-tetrahydro-1-phenyl-1-H-3-benzazepine-7,8-diol. Other compounds useful in the present invention are those described in U.S. Pat. No. 4,477,378 (esters of substituted 8-hydroxy-1-phenyl-2,3,4,5-tetrahydro-1H-3-benzazepines), which is hereby incorporated by reference herein in its entirety.

Ecopipam free base is a benzazepine derivative that is a selective antagonist of the D1 family of receptors. Ecopipam hydrochloride (SCH 39166 HCl; $C_{19}H_{20}NOCl \cdot HCl$) has the chemical structure:

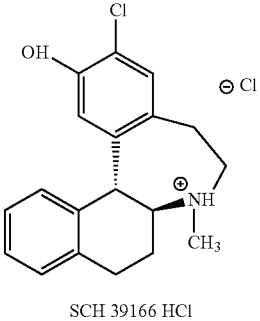

SCH 39166 HCl

The compounds described herein, including those conforming to any formula, can be asymmetric (e.g., having one or more stereocenters). All stereoisomers, such as enantiomers and diastereomers, are intended unless otherwise indicated. The present compounds that contain asymmetrically substituted carbon atoms can be used in mixed form or isolated in optically active or racemic forms. A compound useful in the methods of the invention can have a trans configuration. Methods for preparing optically active forms from optically active starting materials are known in the art. These methods include resolution of racemic mixtures and stereoselective synthesis. For example, one can carry out fractional recrystallization using a chiral resolving acid that is an optically active, salt-forming organic acid. Suitable resolving agents for use in these methods can be, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other useful resolving agents include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Cis and trans geometric isomers of the present compounds are described and may be isolated as a mixture of isomers or as separated isomeric forms. Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Tautomeric forms can be in equilibrium or sterically locked into one form by appropriate substitution.

Compounds of the invention also include all isotopes of atoms occurring in the intermediate or final compounds. Isotopes include those atoms having the same atomic number but different mass numbers. For example, isotopes of hydrogen include tritium and deuterium.

The term "compound," as used herein with respect to any compound conforming to one of the D1/D5 antagonists or partial agonists described above, is meant to include all stereoisomers, geometric isomers, tautomers, and isotopes of the structures referenced (e.g., depicted). All compounds, and all pharmaceutically acceptable salts thereof, can be used in a solvated or hydrated form. In some embodiments, the compounds of the invention (regardless of form; e.g., salts) are "substantially isolated," meaning that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99%, by weight, of a compound of the invention. Methods for isolating compounds and their salts are routine in the art.

As noted, the present methods can be carried out using "pharmaceutically acceptable salts," a term that generally refers to derivatives of the disclosed compounds wherein the parent compound is modified by converting an existing acid or base moiety to its salt form. "Pharmaceutically acceptable" generally encompasses those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit:risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts useful in the methods of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in Remington's Pharmaceutical Sciences, 17th ed., Mack Publishing Company, Easton, Pa., 1985, p. 1418 and the *Journal of Pharmaceutical Science,* 66:2, 1977.

In addition to, or instead of, ecopipam hydrochloride, ecopipam free base may be in the form of another pharmaceutically acceptable salt. Such salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluensulfonic, methanesulfonic, ethane disulfonic, oxalic, isethionic, and the like.

The compounds and compositions disclosed herein are generally and variously useful for treatment of stuttering, which is also variously referred to as stammering. The present compounds and compositions can also be administered for the treatment of stuttering induced as a side effect of a medication; stuttering associated with autism; and stuttering as a result of another disease or condition, such as a sporadic, genetic, or neurodegenerative disorder.

In other embodiments, the compounds and compositions disclosed herein are useful in the treatment of speech and language disorders including expressive language disorder, mixed receptive-expressive language disorder, phonological disorder, and communication disorder not-otherwise-specified (DSM-IV). In any given disorder, there may be impaired production of fluent and comprehensible speech, a phonological disorder, or developmental verbal dyspraxia, in which the coordination and motor control of the speech organs is compromised, or problems with morphology, syntax, semantics, or pragmatics. The term specific language impairment (SLI) is often used as an umbrella term for expressive language disorder, mixed receptive-expressive language disorder, and sometimes phonological disorder. The compounds and compositions disclosed herein can be used to alleviate these disorders.

Patients diagnosed as having Tourette's Syndrome can be explicitly excluded from the present methods.

Subjects are effectively treated whenever a clinically beneficial result ensues. This may mean, for example, a complete or marked resolution of the symptoms of a disorder, a decrease in the frequency, severity, and/or duration of the symptoms, or a slowing of the disorder's progression. Thus, an effective treatment stuttering disorders could manifest as a decrease in the number, duration, frequency and/or intensity of repetitions, prolongations, hesitations and interruptions in the flow of speech observed in the subject. Preferably, there is no significant toxicity in the patient. The level of toxicity, if any, can be determined by assessing a patient's clinical symptoms before and after administering a known amount of a particular composition.

Any of the methods described herein can include a step of identifying a subject (e.g., a patient and, more specifically, a human patient) who has a stuttering disorder. Following diagnosis or in conjunction with diagnostic tests, the methods can then include the step of providing to the subject a compound or composition described herein. "Providing" the compound or composition encompasses a direct administration (e.g., a person practicing the method can directly administer the compound or composition to the patient) as well as indirect administration (e.g., a person practicing the method can give the patient a composition which they then self-administer; a person practicing the method can give the patient a prescription for a composition, which the patient then fills and self-administers). A "therapeutically effective amount" of a composition is an amount that results in marked resolution of the patient's symptoms; a decrease in the frequency, severity, or duration of their symptoms; or a slowing of the disorder's progression. Any of the present methods may also include a step of monitoring the patient (by physical examination and/or interview) to help optimize dosing and scheduling as well as to help predict and optimize outcome.

The methods disclosed herein can be applied to both pediatric and adult subjects.

Regardless of their original source or the manner in which they are obtained, the compounds of the invention can be formulated in accordance with their use. For example, the compounds can be formulated within compositions for administration to a patient (i.e., formulated as pharmaceutical compositions). These compositions can be prepared according to methods well known in the pharmaceutical art and can be administered by a variety of routes. Administration may be topical (including ophthalmic or ocular (e.g., via eye drops) and to mucous membranes (i.e., transmucosal) including buccal, intranasal, vaginal and rectal delivery), pulmonary (e.g., by inhalation or insufflation of powders or aerosols, including by nebulizer), intranasal, epidermal (and transdermal), ocular, or oral. While oral administration is preferable for its convenience, parenteral formulations can also be used, and such formulations can be administered intravenously, intraarterially, subcutaneously, intraperitoneally or intramuscularly (e.g., by injection or infusion). As dopaminergic receptors within the brain are targeted, intracranial (e.g., intrathecal or intraventricular) administration is also contemplated and within the scope of the present methods. Parenteral administration can be in the form of a single bolus dose, or may be, for example, by a continuous perfusion pump. Thus, the formulations include depot formulations, including those that allow for slow-release. For administration by a variety of routes, the compounds described herein can be associated with nano- or microparticles. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

Pharmaceutical compositions useful in the present methods can include an active ingredient (one or more of the compounds described herein) in combination with one or more pharmaceutically acceptable carriers. In making pharmaceutical compositions, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline or a buffered saline such as phosphate-buffered saline) that acts as a vehicle, carrier, or medium for the active ingredient. Thus, the compositions can be in the form of capsules (e.g., soft or hard gelatin capsules), tablets, pills, powders (e.g., sterile packaged powders), lozenges, sachets, cachets, elixirs, suspensions, emulsions, solutions (e.g., sterile injectable solutions), suppositories, syrups, aerosols (as a solid or in a liquid medium), or ointments. These forms can contain, for example, up to about 10% by weight of the active compound. In other embodiments, these forms can contain at least or more than 10% by weight of the active compound (e.g., at least or about 15%, 20%, 25%, 35% or 50% by weight of the active compound). As is known in the art, the type of diluent can vary depending upon the intended route of administration. The resulting compositions can include additional agents, such as coloring, flavoring, or a preservative. The compounds may also be applied to or contained within a drug delivery device such as a pump or patch. The compounds of the invention can be administered alone or in a mixture in the presence of a pharmaceutically acceptable excipient that is selected on the basis of the mode and route of administration. Suitable pharmaceutical excipients as well as pharmaceutical necessities for use in pharmaceutical formulations are described in Remington's Pharmaceutical Sciences (E. W. Martin), a well-known reference text in this field, and in the USP/NF (United States Pharmacopeia and the National Formulary). Other sources are also available to one of ordinary skill in the art. In preparing a formulation, the active compound can be milled to provide the appropriate particle size prior to combining with the other ingredients. If the active compound is substantially water insoluble, it can be milled to a particle size of less than 200 mesh to improve dissolution. If the active compound is substantially water soluble, the particle size can be adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, and other cellulose derivatives. The formulations can additionally include one or more of: a lubricating agent such as talc, magnesium stearate, and mineral oil; a wetting agent; an emulsifying and suspending agent; a preserving agent such as methyl- and propylhydroxy-benzoates; a sweetening agent; and a flavoring agent. The pharmaceutical compositions can be formulated so as to provide quick, sustained, or delayed release of the active ingredient after administration to the patient by employing procedures known in the art.

The compositions can be formulated in a unit dosage form, each dosage containing, for example, from about 0.1 mg to about 500 mg. For example, the present compounds can be formulated with a unit dosage form of about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 250 mg to about 500 mg, from about 300 mg to about 450 mg, from about 300 mg to about 400 mg, or from about 50 mg to about 100 mg of the active ingredient.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 500 mg of the active ingredient of the present invention.

Oral formulations (e.g., tablets, pills, or capsules) can be coated or otherwise compounded to provide a dosage form affording the advantage of prolonged action. For example, the oral formulation can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. Other examples of modified release dosage forms include matrix tablets, with or without additional coating; granules or beads in a capsule, the granules or beads being formulated with or without release modifying excipients or coatings; coated capsules; osmotic pumps, with or without additional coatings; and so on. A variety of materials can be used for such enteric layers or coatings, including a number of polymeric acids and mixtures of polymeric acids with materials such as shellac, cetyl alcohol, and cellulose acetate.

Liquid forms in which the compounds can be incorporated for administration orally or by injection include aqueous solutions, suitably flavored or unflavored syrups, aqueous or oil suspensions, and flavored emulsions with edible oils such as cottonseed oil, sesame oil, soybean oil, coconut oil, or peanut oil, as well as elixirs and similar pharmaceutical vehicles. Oral suspensions can also be formulated in non-aqueous water-miscible vehicles such as propylene glycol or glycerin. Compositions for inhalation or insufflation include solutions and suspensions in pharmaceutically acceptable, aqueous or organic solvents, or mixtures thereof, and powders. In some embodiments, the compositions are administered by the oral or nasal respiratory route for systemic effect. The compositions can be nebulized by use of inert gases and then breathed directly from a nebulizing device. In more extreme situations, the nebulizing device can be attached to a face mask, tent, or intermittent positive pressure breathing machine. Oral and nasal delivery formulations can include solution, suspension, or powdered compositions.

Any of the compositions can be sterilized by conventional sterilization techniques or may be sterile filtered. Aqueous solutions can be packaged for use as is or lyophilized. The lyophilized preparation can then be combined with a sterile aqueous carrier prior to administration. The pH of the compound preparations typically will be between about 3 and 11 (e.g., between about 5 to 9; between about 6 to 7; or between about 7 to 8). It will be understood that use of certain of the foregoing excipients, carriers, or stabilizers could result in the formation of pharmaceutical salts.

The proportion or concentration of the compounds of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. By "about" we mean within 10%, plus or minus, of the specified value.

The therapeutic dosage of the compounds of the present invention can vary according to, for example, the particular use for which the treatment is made, the nature of the formulation, the manner and/or route of administration of the compound, the health and condition of the patient (including, for example, size, weight, surface area, age, and sex, and other drugs being administered), and the judgment of the attending clinician. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, about 1 mg/kg, 2 mg/kg, 5 mg/kg, 10 mg/kg, 20 mg/kg, 50 mg/kg or 100 mg/kg or any range between any two of the recited doses. The dosage is likely to depend on such variables as the type and extent of progression of the disease or disorder, the overall health status of the particular patient, the relative biological efficacy of the compound selected, formulation of the excipient, and its route of administration. Variations in these dosage levels can be adjusted using standard empirical routines for optimization, as is well understood in the art. Administrations can be single or multiple (e.g., a dosage for one patient can be 2- to 3-, or 4-, 6-, 8-, 10-, 20-, 50-, 100-, 150-, or more fold than the dosage for another patient). Encapsulation of the compounds in a suitable delivery vehicle (e.g., polymeric nano- or microparticles or implantable devices) may increase the efficiency of delivery.

The frequency of administration can vary and includes single or multiple doses per day. The compositions can also be taken as needed ("PRN dosing"). The duration of treatment with any composition provided herein can be any length of time from as short as one day to as long as the life span of the host (e.g., many years). For example, a compound can be administered once a day, once a week (for, for example, 4 weeks to many months or years); once a month (for, for example, three to twelve months or for many years); or once a year for a period of five years, ten years, or longer. It is also noted that the frequency of treatment can be variable. For example, the present compounds can be administered once (or twice, three times, etc.) daily, weekly, monthly, or yearly.

The compositions may also be administered along with other treatments, including nonpharmacologic therapies, pharmacologic therapies and surgical treatments. Exemplary nonpharmacologic therapies include reassurance and environmental modifications, identification and avoidance of triggers, and cognitive behavior therapy. Pharmacologic therapies include $\alpha_2$-adrenergic agonists, e.g., including but not limited to clonidine and guanfacine; dopamine receptor-blocking drugs, e.g., including but not limited to haloperidol, pimozide, fluphenazine, olanzapine, risperidone; dopamine-depleting drugs, e.g., including but not limited to tetrabenazine; anti-epileptics, e.g., including but not limited to topiramate; and botulinum toxin injections. Surgical treatments, e.g., deep brain stimulation, may also be used. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Compositions for treating stuttering may also be administered along with (i.e., in addition to) a treatment for a condition such as ADHD, depression, an eating or sleeping disorder, or OCD, if these conditions are present in a given patient. Therapeutic agents useful for ADHD include but are not limited to stimulants such as methylphenidate and non-stimulants such as atomoxetine. Therapeutic agents useful for depression and OCD include but are not limited to selective serotonin reuptake inhibitors (SSRIs), mixed SSRIs (e.g., venlafaxine), monoamine oxidase inhibitors, and atypical anti-depressants such dopamine-reuptake inhibitors (e.g., buproprion). Therapeutic agents useful for sleeping disorders include all barbiturates, all benzodiazepines, and other non-benzodiazepine-sedative-hypnotics (e.g., zolpidem, eszopiclone, zoplicone), and all sedating anti-histamines.

In some embodiments, any one or more of the fused benzazepines as described and exemplified herein may be combined with one or more antipsychotic like olanzapine or haloperidol (Shaygannejad et al., *Int J Prev Med.* 4(Suppl 2):S270-273.). In some embodiments, any one or more of the fused benzazepines as described and exemplified herein may also be combined with one or more other agents that block the inhibitory neurotransmitter, dopamine, including but are not limited to acepromazine, amisulpride, amoxapine, azaperone, benperidol, bromocriptine, bromopride, butaclamol, clomipramine (mild), chlorpromazine, chlorprothixene, clopenthixol, clozapine, domperidone, droperidol, eticlopride, flupenthixol, fluphenazine, fluspirilene, haloperidol, hydroxyzine, iodobenzamide, loxapine, mesoridazine, levomepromazine, metoclopramide, nafadotride, nemonapride, olanzapine, penfluridol, perazine, perphenazine, pimozide, prochlorperazine, promazine, quetiapine, raclopride, remoxipride, risperidone, ropinirole, spiperone, spiroxatrine, stepholidine, sulpiride, sultopride, tetrahydropalmatine, thiethylperazine, thioridazine, thiothixene, tiapride, trifluoperazine, trifluperidol, triflupromazine and ziprasidone In some embodiments, any one or more of the fused benzazepines as described and exemplified herein may be combined with one or more benzodiazepine or a nonbenzodiazepine γ-aminobutyric acid modulator, including but not limited to barbiturates, benzodiazepines, carisoprodol, chloral hydrate, etaqualone, etomidate, glutethimide, kava, methaqualone, muscimol, neuroactive steroids, z-drugs, propofol, scullcap, valerian, theanine, volatile/inhaled anaesthetics, bicuculline, cicutoxin, flumazenil, furosemide, gabazine, oenanthotoxin, picrotoxin, Ro15-4513, thujone, baclofen, GBL, propofol, GHB, phenibut, phaclofen, saclofen, deramciclane, hyperforin, tiagabine, gabaculine, phenelzine, valproate, vigabatrin, lemon balm, pregabalin, gabapentin, GABA (itself), L-glutamine, picamilon, progabide and a cyclopyrrolone like pagoclone.

In some embodiments, any one or more of the fused benzazepines as described and exemplified herein may be combined with one or more benzodiazepine including but not limited to adinazolam, alprazolam, chlordiazepoxide, climazolam, clonazepam, clorazepate, diazepam, estazolam, flunitrazepam, flurazepam, halazepam, loprazolam, lormetazepam, lorazepam, midazolam, nimetazepam, nitrazepam, oxazepam, prazepam, temazepam and triazolam.

In some embodiments, any one or more of the fused benzazepines as described and exemplified herein may be combined with one or more nonbenzodiazepines. Suitable nonbenzodiazepines are imidazopyridines, including but not limited to zolpidem, alpidem, necopidem and saripidem, pyrazolopyrimidines, including but not limited to zaleplon, divaplon, fasiplon, indiplon, lorediplon, ocinaplon, panadiplon and taniplon, cyclopyrrolones, including but not limited to eszopiclone, zopiclone, pagoclone, pazinaclone, suproclone and suriclone, β-carbolines, including but not limited to abecarnil, gedocarnil and ZK-93423 and other drugs including but not limited to CGS-9896, CGS-20625, CL-218,872, ELB-139, GBLD-345, L-838,417, NS-2664, NS-2710, pipequaline, RWJ-51204, SB-205,384, SL-651, 498, SX-3228, TP-003, TP-13, TPA-023 and Y-23684.

In some embodiments, any one or more of the fused benzazepines as described and exemplified herein may be combined with one or more anti-depressant drugs, including but not limited to one or more selective serotonin reuptake inhibitors (SSRIs), serotonin-norepinephrine reuptake inhibitors (SNRIs), serotonin modulators and stimulators (SMSs), serotonin antagonists and reuptake inhibitors (SARIs), norepinephrine reuptake inhibitors (NRIs), tricyclic antidepressants (TCAs), tetracyclic antidepressants (TeCAs) and monoamine oxidase inhibitors (MAOIs).

In some embodiments, any one or more of the fused benzazepines as described and exemplified herein may be combined with one or more selective serotonin reuptake inhibitors including but not limited to alaproclate, citalopram, dapoxetine, escitalopram, femoxetine, fluoxetine, fluvoxamine, ifoxetine, indalpine, omiloxetine, panuramine, paroxetine, pirandamine, RTI-353, sertraline and zimelidine.

In some embodiments, any one or more of the fused benzazepines as described and exemplified herein may be combined with one or more active metabolites of selective serotonin reuptake inhibitors including but not limited to desmethylcitalopram, desmethylsertraline, didesmethylcitalopram and seproxetine ((S)-norfluoxetine). In some embodiments, any one or more of the fused benzazepines as described and exemplified herein may be combined with one or more combined serotonin reuptake inhibitors and serotonin receptor ligands including but not limited to cianopramine, litoxetine, lubazodone, SB-649,915, trazodone, vilazodone and vortioxetine. In some embodiments, any one or more of the fused benzazepines as described and exemplified herein may be combined with one or more other drugs with serotonin reuptake inhibitor activity including but not limited to 3-MeO-PCP, 4-MeO-PCP, delucemine, mesembrenone, mesembrine, methoxetamine, roxindole, dextromethorphan, dimenhydrinate, diphenhydramine, ketamine, mepyramine/pyrilamine, methadone and propoxyphene.

In some embodiments, any one or more of the fused benzazepines as described and exemplified herein may be combined with one or more serotonin-norepinephrine reuptake inhibitor (SNRIs) including but not limited to desvenlafaxine, duloxetine, levomilnacipran, milnacipran, tofenacin and venlafaxine. In some embodiments, any one or more of the fused benzazepines as described and exemplified herein may be combined with one or more serotonin modulators and stimulators (SMSs) including but not limited to vilazodone and vortioxetine. In some embodiments, any one or more of the fused benzazepines as described and exemplified herein may be combined with one or more serotonin antagonists and reuptake inhibitors (SARIs) including but not limited to etoperidone, trazodone and nefazodone.

In some embodiments, any one or more of the fused benzazepines as described and exemplified herein may be combined with one or more norepinephrine reuptake inhibitors (NRIs) including but not limited to reboxetine, viloxazine and atomoxetine. In some embodiments, any one or more of the fused benzazepines as described and exemplified herein may be combined with one or more tricyclic antidepressants (TCAs) including but not limited to amitriptyline, butriptyline, clomipramine, desipramine, dosulepin, doxepin, imipramine, iprindole, lofepramine, melitracen, nortriptyline, protriptyline, trimipramine, opipramol, tianeptine, and amineptine. In some embodiments, any one or more of the fused benzazepines as described and exemplified herein may be combined with one or more tetracyclic antidepressants (TeCAs) including but not limited to amoxapine, maprotiline, mianserin, mirtazapine, setiptiline and mianserin.

In some embodiments, any one or more of the fused benzazepines as described and exemplified herein may be combined with one or more monoamine oxidase inhibitors (MAOIs) including but not limited to benmoxin, caroxazone, eprobemide, hydracarbazine, isocarboxazid, iproclozide, iproniazid, isoniazid, ladostigil, mebanazine, metralindole, minaprine, moclobemide, nialamide, octamoxin, phenelzine, pheniprazine, phenoxypropazine, pirlindole, pivalylbenzhydrazine, pivhydrazine, procarbazine, rasagiline, safrazine, selegiline, tranylcypromine, and toloxatone.

In some embodiments, any one or more of the fused benzazepines as described and exemplified herein may be combined with one or more anti-anxiety drugs including but not limited to afobazole, azapirones, like buspirone and tandospirone, batbetuates, bromantane, emoxypine, hydroxyzine, mebicar, pregabalin, selank, validol, beta blockers BNC210, CL-218,872, L-838,417, SL-651,498, S32212 and PH94B. In some embodiments, any one or more of the fused benzazepines as described and exemplified herein may be combined with one or more herbal treatments including but not limited to *Garcinia indica* (Kokum), *Scutellaria lateriflora, Coriandrum sativum* (Cillantro), *Salvia elegans* (Pineapple Sage) and Cannabidiol (a cannabinoid found in marijuana).

In some embodiments, any one or more of the fused benzazepines as described and exemplified herein may be combined with one or more Catechol-O-Methyl-Transferase (COMT) inhibitors including but not limited to entacapone, tolcaponeand nitecapone. In some embodiments, any one or more of the fused benzazepines as described and exemplified herein may be combined with one or more Vesicular Monoamine Transporter-2 (VMAT-2) inhibitors including but not limited to dihydrotetrabenazine (DTBZ), GZ-793A, ketanserin, lobeline, pramipexole, reserpine and tetrabenazine.

The compounds and compositions described herein can be packaged in suitable containers together with information and instructions for use (e.g., a label, other printed material, or information convey by other media (e.g., audio or visual media) as a therapy to treat a stuttering disorder. Accordingly, packaged products (e.g., sterile containers containing one or more of the compounds described herein and packaged for storage, shipment, or sale at concentrated or ready-to-use concentrations) and kits, including at least one compound of the invention and instructions for use as described herein, are also within the scope of the invention. A product can include a container (e.g., a vial, jar, bottle, bag, or the like) containing one or more compounds of the invention. In addition, an article of manufacture further may include, for example, packaging materials, instructions for use, syringes, buffers or other control reagents for treating or monitoring the condition for which prophylaxis or treatment is required. Instructions for use can be associated with the container (e.g., affixed to the container) and can describe the manner in which the compound therein should be administered (e.g., the frequency and route of administration), indications therefor, and other uses. The compounds can be ready for administration (e.g., present in dose-appropriate units), and may include a pharmaceutically acceptable adjuvant, carrier or other diluent and/or an additional therapeutic agent as described above. Alternatively, the compounds can be provided in a concentrated form with a diluent and instructions for dilution.

For clarity and to obviate an excessively long specification, certain features of the invention are described in the context of separate embodiments. The inventors intend, and one of ordinary skill in the art will appreciate, that a feature described in the context of one embodiment can be included in another embodiment, in addition to or in place of, the particular feature(s) described there. In other words, features described in separate embodiments can also be used in combination in a single embodiment that is distinct from those specifically set out herein. Thus, various features of the invention that are described in the context of a single embodiment, for the purpose of reasonable brevity, can also be provided separately or in any suitable sub-combination.

EXAMPLES

Example 1: Safety, Tolerability, and Activity of Ecopipam in Adult Patients

A clinical program was carried out to test the safety, tolerability, and activity of ecopipam in adult patients with Tourette's Syndrome. A multicenter, open-label, nonrandomized study in 25 to 30 subjects was conducted to assess the activity and safety of ecopipam in subjects with TS. Eligible subjects were started on an 8-week treatment period with ecopipam and were seen in the clinic every other week (with telephone contacts on the alternate weeks). Assessment was performed at each visit. A follow-up visit was conducted via telephone at Week 10 to record any adverse events. Ecopipam was administered daily before bedtime at 50 mg/day for Week 1 and Week 2 and at 100 mg/day for Weeks 3-8. This treatment regimen is within the scope of the present invention; the compositions and various formulations described herein can be administered as described in this Example.

The demographics of the study population were as follows: eighty three percent of the subjects were male (15 out of 18); fifteen were Caucasian, two were African-American, and one was an Asian/Pacific Islander. All subjects reported at least one adverse event (AE). There were no serious adverse events (i.e., requiring medical intervention; AEs). Four patients reported AEs that were rated as severe and included the following: sedation, insomnia, decreased appetite, hypersensitivity, cold sweat, and feeling jittery. The following AEs were rated mild to moderate and were reported in more than three subjects: fatigue, insomnia, nausea, sedation, headache, restlessness, anxiety, muscle twitching, dysphoria, and sleeplessness. These side effects are similar to those seen in other studies with ecopipam and were not unexpected.

Sporadic changes in lab tests were observed, but none were of clinical significance. Likewise, there were no clinically significant changes in vital signs.

Example 2: Placebo-Controlled, Double-Blind, Randomized Clinical Trial for Stuttering Results are obtained from a placebo-controlled, double-blind, randomized clinical trial for stuttering, as described below.

Patients: Healthy subjects (as shown by physical exam, vital signs, and blood/urine tests) between ages 7 and 60 years with moderate to severe stuttering of either gender are included as subjects in the study. Exclusion criteria will be (1) recent history of significant cardiovascular, renal or respiratory disease; or (2) having signs of active depression or other severe mental illness. All subjects must sign an informed consent form or have one signed by the patient or a parent/guardian.

Screening-Visit (Day −28 to Day −14): At the screening visit the following safety analyses will be performed: screening medical history, Columbia Suicide Severity Rating Scale (C-SSRS) and the Beck Depression Inventory (BDI), vital signs, physical exam and laboratory tests of hepatic and renal function, urine analysis, a drug screen and a urine pregnancy test (for women of child-bearing potential only).

Ratings will include a video/audio taping of objective stuttering measurements (percentage of syllables stuttered during conversation, percentage of syllables stuttered during reading aloud, and the duration of the stuttered events) to assess the individual's fluency via the Stuttering Severity Instrument-Version IV (SSI-IV). This is a validated rating scale which includes speaking to another individual for approximately 10 minutes in a typical conversation and reading a magazine or a newspaper article aloud. Each rating session will be videotaped and audio-taped. A Clinical Global Impression Scale-Severity (CGI-S) will also be performed at this visit by the clinician and the subject. Each subject will complete a participant questionnaire which will include the history and development of stuttering, the treatment, and family history of stuttering. The subject will also complete a subjective stuttering scale (SSS) that will contain fifteen items concerning their stuttering. Eligible subjects will not have a decrease in the SSI-IV score of 20% between the screening and baseline visits.

Baseline-Visit (Week 1): Safety assessments including the following will be performed: C-SSRS, BDI, vital signs and a urine pregnancy test (for women of child-bearing potential only). Each subject will be asked to complete the SSS, CGI-S and participate in the audio/video taping of objective stuttering measurements as rated using the SSI-IV. The clinician will also perform a CGI-S.

Dosing: At the Baseline Visit eligible subjects will be randomly assigned to receive either ecopipam (50 mg/day or 100 mg/day) or placebo, in a double-blind manner. In some studies, a period of up-titration starting at the Baseline Visit may be done to determine an optimum dose. The drug can be formulated and administered at any therapeutically effective dose and according to any formulation, dose and dosing regimen described herein.

For example, the compound administered (e.g., a D1/D5 receptor antagonist, for example, ecopipam) can be formulated for oral or parenteral (e.g., subcutaneous) delivery (e.g., formulated in a unit dosage form of about 0.01 mg/kg to about 500 mg/kg (e.g., about 0.01 mg/kg to about 50 mg/kg; about 0.01 mg/kg to about 5 mg/kg; or about 0.1 mg/kg to about 5 mg/kg)). The formulation may be an immediate release or controlled release formulation. With respect to daily dosages, the compound, e.g., ecopipam, can be administered at a dose of about 5 to about 100 mg/day in multiple doses per day. In some embodiments, the dose is adjusted based on age and body weight. For example, when children are treated, the dose may need to be at the low end of the dose range, (for example at the low end of the dose per kg or dose per day range), or further adjusted downward. In some embodiments, the drug is administered orally once per day. The administration can occur once per day or in divided doses, and any of the treatments described herein can include a step of administering a "second" composition or therapy for treating the stuttering, for example, any of the pharmaceutical, surgical or non pharmacologic (e.g., behavioral) treatments described herein. The treatment can also encompass administration of a compound as described herein together with a behavioral therapy, surgical therapy, or distinct pharmaceutical therapy.

Clinic Visits (Week 2, 3, 4, 5): At weekly intervals each subject will be evaluated for tolerability and medication compliance and any unused medication will be collected. The C-SSRS and BDI will be performed. All adverse events will be recorded. Each subject will complete the SSS, CGI-S and participate in the audio/video taping of objective stuttering measurements the SSI-IV. A CGI-S will be performed by a clinician as well.

Final Clinic Visit (Week 6 or Early Termination): At the final visit each subject will be evaluated for tolerability and medication compliance and any unused medication will be collected. A speech sample (SSI-IV) will be measured by using the objective stuttering measurement (SSI-IV) which will include speaking to another individual for approximately 10 minutes in a typical conversation and reading a magazine or a newspaper article aloud. Each subject will be asked to complete the subjective stuttering questionnaire (SSS) and a Clinical Global Impression-Improvement and Severity will be performed by the clinician and the subject. The Columbia Suicide Severity Rating Scale will be performed. If appropriate, down titration study medication will be dispensed. Lastly, a blood draw will also be obtained to assess for any significant metabolic changes and a urine pregnancy test (for women of child-bearing potential only). All adverse events will be recorded.

Statistical analyses of the data may be performed, for example, according to Maguire et al. 2010). For example, for continuous variables that satisfied the parametric assumptions, analysis of variance (ANOVA) with effects for treatment and pooled center are used. For nonparametric continuous variables, the median test or a ranked ANOVA is applied. If there is a significant difference at baseline between the treatment groups, the baseline values are added to the model as a covariate, and the appropriate P value from the analysis based on assumption testing was presented (i.e., either ANOVA or ranked ANOVA). For categorical variables, a Cochran-Mantel Haenszel (CMH) test is used, controlling for pooled center. For categorical variables with inherent ordering to the categories, a CMH row means score test is used. Efficacy analyses may be performed using the last-observation-carried-forward (LOCF) data set. If data are missing at a given visit, the most recent prior data point collected is carried forward. However, pretreatment data are not carried forward into the treatment data.

In some embodiments, the primary end point is captured at the week 8 visit, however, week 4 and pooled time points are also assessed. Because of the inherent variability of stuttering severity, the average of the 2 pretreatment outcomes (the screening and baseline data) is compared with the average of the 2 on-treatment outcomes (the week 4 and week 8 data) for most variables.

Ecopipam's ability to improve symptoms of stuttering is demonstrated by a significant reduction in the SSI-IV rating scale A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a subject who stutters or who has been diagnosed as having a stuttering disorder, the method comprising:

(a) identifying a subject in need of treatment; and
(b) administering to the subject a therapeutically effective amount of a composition comprising, ecopipam or a pharmaceutically acceptable salt, solvate, hydrate, structural analog, polymorph or a mixture thereof.

2. The method of claim 1, wherein the subject is a human male.

3. The method of claim 1, wherein the subject is not older than 17 years.

4. The method of claim 1, wherein the subject is considered to be free from attention-deficit-hyperactivity disorder, depression, Tourette's Syndrome, and obsessive-compulsive disorder.

5. The method of claim 1, wherein the stuttering is associated with a developmental stuttering disorder.

6. The method of claim 1, wherein the stuttering is associated with a neurogenic or psychogenic disorder.

7. The method of claim 1, wherein the composition comprises ecopipam or a pharmaceutically acceptable salt, solvate, hydrate or polymorph thereof.

8. The method of claim 1, wherein the composition comprises ecopipam or a pharmaceutically acceptable salt thereof.

9. The method of claim 1, wherein the composition is formulated for oral delivery.

10. The method of claim 1, wherein the composition is formulated to administer a dose of about 0.01 mg/kg to about 500 mg/kg.

11. The method of claim 1, wherein the composition is formulated to administer a dose of about 0.01 mg/kg to about 50 mg/kg; about 0.01 mg/kg to about 5 mg/kg; or about 0.1 mg/kg to about 5 mg/kg.

12. The method of claim 1, wherein the composition is formulated to administer a dose of 5-100 mg/day.

13. The method of claim 1, wherein the composition is administered at a dose of from 0.1 mg to 50 mg, from 0.1 mg to 40 mg, from 0.1 mg to 20 mg, from 0.1 mg to 10 mg, from 0.2 mg to 20 mg, from 0.3 mg to 15 mg, from 0.4 mg to 10 mg, from 0.5 mg to 1 mg; from 0.5 mg to 100 mg, from 0.5 mg to 50 mg, from 0.5 mg to 30 mg, from 0.5 mg to 20 mg, from 0.5 mg to 10 mg, from 0.5 mg to 5 mg; from 1 mg from to 50 mg, from 1 mg to 30 mg, from 1 mg to 20 mg, from 1 mg to 10 mg, from 1 mg to 5 mg; from 5 mg to 50 mg, from 5 mg to 20 mg, from 5 mg to 10 mg; from 10 mg to 100 mg, from 20 mg to 200 mg, from 30 mg to 150 mg, from 40 mg to 100 mg, from 250 mg to 500 mg, from 300 mg to 450 mg, from 300 mg to 400 mg, or from 50 mg to 100 mg.

14. The method of claim 1, wherein the composition is formulated to dose once, twice, or three times.

15. The method of claim 1, wherein the composition is administered along with a second treatment for treating the stuttering disorder.

16. The method of claim 15, wherein the composition is, wherein the second treatment is a behavioral, surgical, or pharmaceutical therapy.

17. The method of claim 1, wherein the composition is administered is adjusted depending on age and body weight.

18. The method of claim 1, wherein the composition is formulated in a unit dosage form.

19. The method of claim 1, wherein the composition is formulated as a capsule, tablet, pills, powder, or syrup.

20. The method of claim 1, wherein the composition is formulated so as to provide quick, sustained, or delayed release.

* * * * *